United States Patent [19]

Pallanck

[11] Patent Number: 4,564,405
[45] Date of Patent: Jan. 14, 1986

[54] PYX PURIFICATION TECHNIQUE

[75] Inventor: Robert G. Pallanck, Stafford Springs, Conn.

[73] Assignee: Ensign-Bickford Industries, Inc., Simsbury, Conn.

[21] Appl. No.: 620,181

[22] Filed: Jun. 13, 1984

[51] Int. Cl.$^4$ .............................................. C06B 45/02
[52] U.S. Cl. .................................... 149/21; 149/2; 149/92; 149/111; 546/307; 546/334
[58] Field of Search .................... 149/21, 2, 92, 111; 546/307, 334

[56] References Cited

U.S. PATENT DOCUMENTS

| | | | |
|---|---|---|---|
| 3,678,061 | 7/1982 | Coburn | 149/82 X |
| 4,361,450 | 11/1982 | Munson | 149/38 X |
| 4,428,292 | 1/1984 | Riggs | 149/39 X |
| 4,497,251 | 2/1985 | Rucker | 102/202.6 |
| 4,519,313 | 5/1985 | Leidel | 102/307 |

Primary Examiner—Stephen J. Lechert, Jr.
Attorney, Agent, or Firm—Hayes & Reinsmith

[57] ABSTRACT

The formation of two crystalline forms of 2,6-bis (picrylamino)-3,5 dinitropyridine is accomplished by a purification method wherein needle-shaped crystals of 2,6-bis (picrylamino)-3,5 dinitropyridine are dissolved in dimethyl sulfoxide to form an adduct compound. Dissociating the adduct compound forms different crystalline structures of 2,6-bis (picrylamino)-3,5 dinitropyridine having improved properties.

17 Claims, 3 Drawing Figures

100μm

100μm

100μm

PYX PURIFICATION TECHNIQUE

This invention relates to two molecular forms of 2,6-bis(picrylamino)-3,5-dinitropyridine having improved physical and handling properties as well as a novel process of synthesizing 2,6-bis(picrylamino)-3,5 dinitropyridine, a high temperature stable explosive and propellant ingredient.

BACKGROUND OF THE INVENTION

It has been known that crystal shape and size distribution of explosive materials are important parameters which affect the product quality handling characteristics and product safety. Because of such facts, explosive materials are subjected to various processing techniques to facilitate fabrication of explosive devices and ensure optimum product quality. The techniques are designed to modify granulation and crystal morphology and thereby improve the powder flow, bulk and pressed density and dusting properties of explosive. Customary modification techniques known in the art, which are either used alone or in combination, are grinding, adding binders and/or sensitizers and recrystallizing the explosive material.

OBJECTS OF THE INVENTION

It is an object of this invention to provide a facile and economical method by which improved thermally stable and increased impact sensitive particle forms of 2,6-bis(picrylamino)-3,5-dinitropyridine are formed by the processing of needle-shaped 2,6-bis(picrylamino)-3,5-dinitropyridine with dimethyl sulfoxide.

It is another object of this invention to provide a method for altering particle size and particle configuration of needle-shaped 2,6-bis(picrylamino)-3,5-dinitropyridine thereby to improve handling and processing characteristics.

It is still another object of this invention to provide a cubic crystalline particle structure of PYX.

It is a further object of this invention to provide for an agglomerate crystalline particle structure of 2,6-bis(-picrylamino)-3,5-dinitropyridine.

Other objects will be in part obvious and in partly pointed out in more detail hereinafter.

A better understanding of the objects, advantages, features, properties and relations of the invention will be obtained from the following detailed description and photomicrographs which set forth certain illustrative embodiments and are indicative of the various ways in which the principles of the invention are employed.

SUMMARY OF THE INVENTION

This invention provides for two novel crystalline forms of 2,6-bis(picrylamino)-3,5-dinitropyridine and a method for processing the two modified crystalline forms of 2,6-bis(picrylamino)-3,5-dinitropyridine (herein after referred to as PYX). According to this invention, needle-shaped crystals of synthesized PYX are treated with adduct forming compound dimethyl sulfoxide (herein after referred to as DMSO) to form an intermediate PYX/DMSO adduct compound which is then dissociated into either of two crystalline forms—cubic or agglomerate.

DETAILED DESCRIPTION OF THE INVENTION

Specifically, the objects of this invention may be accomplished by the regeneration of cubic or agglomerate crystalline forms of PYX from an adduct which PYX forms with dimethyl sulfoxide (commonly known as DMSO). The adduct or addition compound is formed by the addition of about one molar proportion of PYX to about three moles of solvent DMSO used, with the preferred concentration ratio being about 1:29 of PYX to DMSO at a temperature of 100°–110° C.

Figure 1:
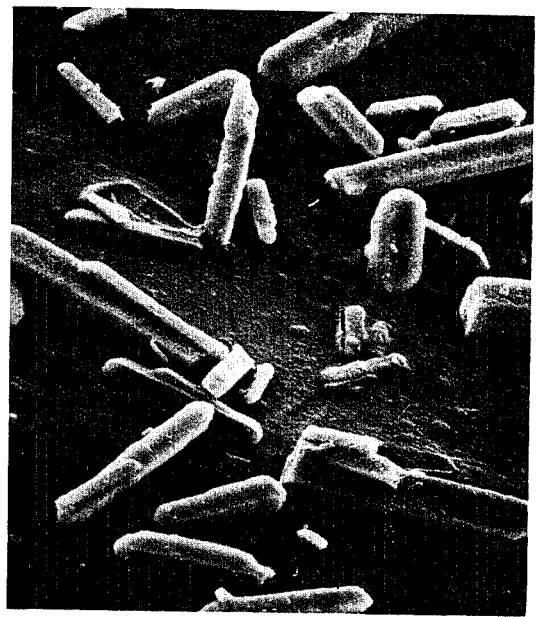
FIG. 1 is a photomicrograph of needle-shaped PYX crystals.

A supply of crude PYX having a fine needle-shaped particle crystalline structure, as pictured in FIG. 1, is completely dissolved in solvent DMSO at an elevated temperature. The preferred temperature range is 100°–110° C., although different temperature ranges may be employed where solubility relations are favorable. The resultant solution is then cooled to a temperature of 20°–30° C. to obtain a slurry of PYX/DMSO adduct crystals. The slurry is then filtered to remove excess DMSO from the adduct crystals, and the excess DMSO may be recycled for further use in dissolving the crude PYX particles. At this point the PYX/DMSO adduct is dissociated by employment of one of several methods. The choice of the method will determine the shape of the resultant PYX crystals.

The agglomerate form of PYX is obtained by dissociating the slurry of the adduct crystals in a solvent miscible with DMSO but in which PYX has substantially no solubility. The solvents used include water and various organic solvents or mixtures thereof, with preference for solvents such as acetone, methanol and mixtures thereof. An acetone boil-up procedure forms an agglomerate of spherical particles as pictured by FIG. 2.

The cubic crystalline form of modified PYX is obtained by subjecting the adduct crystals to heat, vacuum or combination thereof. The cubic crystal structure is pictured in FIG. 3.

PYX purified or synthesized in the manner described above is superior to the commercial needle-shaped form of PYX because of its improved thermal stability and its increased density. Moreover, because of its relatively uniform particle size and mixture, it is easy to pour and handle and has a reduced tendency to acquire a static charge.

The purification of PYX through its adduct with DMSO is less expensive than conventional methods of purification because recovery of PYX is more complete, the apparatus is simpler and the processing is accomplished in a few steps. Moreover, DMSO may be recovered from the filteration step, and reused in recycled dissolving the needle-shaped PYX crystals. The method also provides for the modified PYX crystals to be recovered in 80% yield or better from their solution in DMSO.

The DMSO recovered from the filteration step can be recycled and subsequently reused without adversely affecting the thermal stability or particle size distribution of the modified PYX forms. Table 1 illustrates the results of four DMSO recycling tests:

TABLE 1
RECYCLE OF DMSO IN PYX[a] RECRYSTALLIZATION[b]

| Trial | # of Times DMSO Recycled | % DMSO Recovered | % PYX Recovered | %[c] Wt. Loss | Coulter Part. Size Dist % microns |
|---|---|---|---|---|---|
| 1 | 0 | 85 | 88 | 4.3 | 25%–28 50%–20 75%–12 |
| 2 | 1 | 84 | 89 | 5.5 | 25%–32 50%–22 75%–12 |
| 3 | 2 | 85 | 88 | 4.7 | 25%–36 50%–26 75%–15 |
| 4 | 3 | 85 | 89 | 4.5 | 25%–42 50%–25 75%–14 |

[a]2, 6-bis (picrylamino)-3, 5 dinitropyridine = PYX
[b]PYX isolated from DMSO via acetone boil-up
[c]TGA conditions: 50° C. to 330° C. at 20° C./min., held 1 hour at 330° C.

The control of the mean diameter and size distribution of the particles of the final recrystallized product is accomplished by careful choice of adduct formation and dissociation parameters. Variations in the composition and volume of the solvent and duration of the dissociation period or method will determine the size distribution and mean diameter of the resultant particles. Typical particle sizing of each form of PYX as analyzed by a Coulter Particle Size Analyzer are shown in the following Table 2:

TABLE 2
COULTER PARTICLE SIZE MEASUREMENT

| PYX Particle Form | 25% Level (μ) | 50% Level (μ) | 75% Level (μ) |
|---|---|---|---|
| Needle | 40.8 | 30.6 | 22.4 |
| Cubic | 129.0 | 92.0 | 63.0 |
| Agglomerate | 48.5 | 37.8 | 28.9 |

As seen, the particle size of the cubic crystal is the largest, followed by that of the agglomerate crystal, with the needle-shaped being the smallest.

Vertical impact sensitivity measurements indicate that the modified PYX crystalline forms are more sensitive to initiation by impact or shock than the usual needle-shaped form. Table 3 give the results of impact sensitivity tests performed on an USBM impact tester (modified ASTM E-L-80-79):

TABLE 3
VERTICAL IMPACT SENSITIVITY OF PYX

| PYX Particle Form | Height (cm) |
|---|---|
| Needle | 84.9 |
| Cubic | 81.8 |
| Agglomerate | 77.2 |

Additionally, bulk density measurements were taken on the three forms of PYX by measuring 5 gram samples of each material in a calibrated volumetric cylinder under constant vibration for 4 minutes. The results, shown in the following Table 4, indicate the higher bulk density of the cubic and agglomerate forms of PYX.

TABLE 4
PYX BULK DENSITY

| PYX Particle Form | Bulk Density (g/cc) |
|---|---|
| Needle | 0.69 |
| Cubic | 0.79 |
| Agglomerate | 0.82 |

Thermal stability testing proved the modified forms of PYX as being more temperature stable than the needle-shaped form. Thermal stability as measured by thermal gravemetric analysis on a Perken-Elmer TG-2 thermal analyzer, is shown in the following Table 5:

TABLE 5
Thermal Stabilty of PYX

| PYX Particle Form | % Weight Loss[a] |
|---|---|
| Needle | 12.00 |
| Cubic | 2.93 |
| Agglomerate | 5.61 |

[a]Conditions - Ambient to 330° C. @ 20° C./m, hold 1 hour @ 330° C. in air.

The following examples are intended to illustrate the process and novel products of this invention and should not be construed as a limitation of the scope or variations thereof.

EXAMPLE 1 (AGGLOMERATE)

Figure 2:
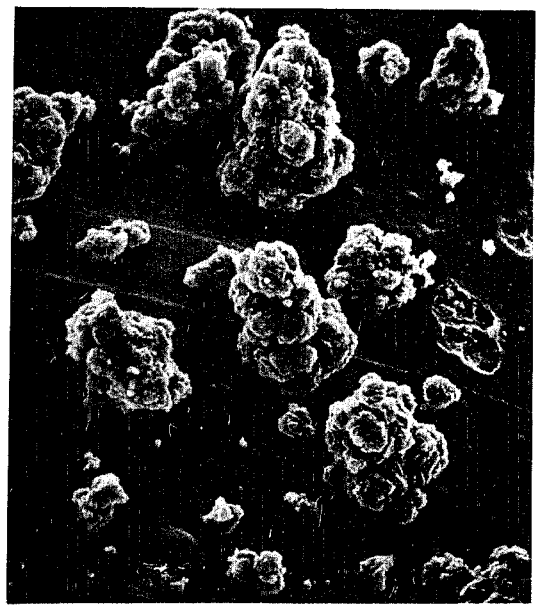
FIG. 2 is a photomicrograph of agglomerate PYX crystals of this invention.

A jacketed, 12 liter glass reaction flask equipped with bottom outlet, mechanical stirrer and a therometer was charged with 4.5 liters dimethyl sulfoxide-(DMSO) and 1125 g. PYX composed of fine needle shaped crystals (FIG. 1). The solution was heated to 95° C., held for 15 minutes to completely dissolve the PYX, then cooled to 23° C. over 40 minutes to form crystals of an adduct of PYX and DMSO. The cooled slurry of adduct in excess DMSO was filtered and the crystals of adduct were washed two times with 750 ml. acetone at room temperature to remove excess DMSO from the surface of the adduct crystals. The adduct crystals were then returned to the 12 liter flask and slurried with 6.0 liters of acetone at reflux for 0.5 hour to dissociate the adduct and extract out the DMSO. The hot slurry of pure PYX was filtered and the PYX crystals washed with 200 ml. acetone to remove last traces of DMSO from the surface of the crystals. The crystals were air dried for 4 hours at room temperature, 16 hours at 70° C. and 7 hours at 100° C. to obtain 1020 g. (91% yield) pure PYX in the form of agglomerated crystals (FIG. 2).

EXAMPLE 2 (CUBIC)

Figure 3:
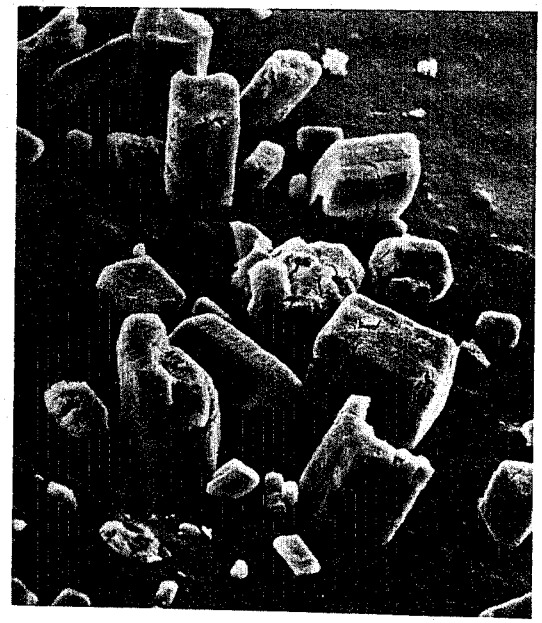
FIG. 3 is a photomicrograph of cubic shaped PYX crystals of this invention.

A jacketed, 12 liter glass reaction flask equipped with a bottom outlet, mechanical stirrer and a therometer was charged with 6.0 liters dimethyl sulfoxide-(DMSO) and 1500 g. PYX composed of fine needle shaped crystals (FIG. 1). The solution was heated to 95° C., held for 15 minutes to completely dissolve the PYX, then cooled to 24° C. over 45 minutes to form crystals of an adduct of PYX and DMSO. The cooled slurry of adduct in excess DMSO was filtered and the crystals of adduct were washed two times with 1.0 liter of acetone at room temperature to remove excess DMSO from the surface of the adduct crystals. The crystals were dried for 17 hours at 140° C. under 0.4 mm Hg vacuum to obtain 1315 g. (88% yield) pure PYX in the form of cubic crystals (FIG. 3).

EXAMPLE 3

Recrystallization of PYX with Recycled DMSO

A one liter Erlenmeyer flask equipped with magnetic stirrer and thermometer was charged with 150 g. crude PYX, 420 ml. DMSO recovered from a previous recrystallization and 80 ml. of fresh dimethyl sulfoxide. The resulting slurry was filtered and the filtrate collected to obtain 420 ml. The crystals were washed two times with 75 ml. acetone, then slurried for one half hour in 800 ml. of boiling acetone. The slurry was filtered and the crystals rinsed with 100 ml. of acetone. The crystals were air dried for 3 hours at room temperature, then oven dried 8 hours at 105° C. to obtain 120 g. (90% yield) PYX.

Thus, as can be seen from the foregoing, the two unique crystalline forms of 2,6-bis(picrylamino)-3,5-dinitropyridine provide increased impact sensitivity and improved thermal stability as compared to the needle-shaped form, while being produced under a simple and economic process. As will be appreciated, the modified crystalline shape and size distribution provide for enhanced powder flow, bulk density and reduced dusting properties.

As will be apparent to persons skilled in the art, various modifications, adaptations and variations of the foregoing specific disclosure can be made without departing from the teachings of this invention.

I claim:

1. A process for synthesizing crystals of 2,6-bis(picrylamino)-3,5-dinitropyridine, the process comprising the steps of:
   (a) dissolving 2,6-bis(picrylamino)-3,5-dinitropyridine in dimethyl sulfoxide to form an adduct of 2,6-bis(picrylamino)-3,5 dinitropyridine and dimethyl sulfoxide;
   (b) cooling the resultant solution to obtain a slurry of dimethyl sulfoxide and 2,6-bis(picrylamino)-3,5 dinitropyridine adduct;
   (c) filtering the slurry to remove excess dimethyl sulfoxide; and
   (d) dissociating the dimethyl sulfoxide and 2,6-bis(picrylamino)-3,5 dinitropyridine adduct to form particles of 2,6-bis(picrylamino)-3,5 dinitropyridine.

2. The process of claim 1 wherein said step of dissociating is carried out by slurrying the adduct in a solvent miscible with dimethyl sulfoxide.

3. The process of claim 2 wherein the solvent is selected from the group consisting of water, acetone, methanol and mixtures thereof.

4. The process of claim 1 wherein said step of dissociating is carried out by subjecting the adduct to heat.

5. The process of claim 1 wherein said step of dissociating is carried out by subjecting the adduct to a vacuum.

6. The process of claim 1 wherein said step of dissociating is carried out by a combination of heat and vacuum.

7. A cubic crystal particle form of 1,2,6-bis(picrylamino)-3,5 dinitropyridine produced in accordance with the process of claim 1, 4, 5, or 6.

8. A agglomerate crystal particle form of 2,6-bis(picrylamino)-3,5 dinitropyridine produced in accordance with the process of claim 1, 2 or 3.

9. The process of claim 1 in which further comprises the step of recycling the dimethyl sulfoxide recovered from after the filteration step for use in dissolving the crude 2,6-bis(picrylamino)-3,5 dinitropyridine.

10. The process of claim 1 or 9 which further comprises the step of washing 2,6-bis(picrylamino)-3,5 dinitropyridine with a nitric acid solution.

11. The process of claim 1 or 10 wherein the particle size of 2,6-bis(picrylamino)-3,5 dinitropyridine is controlled.

12. A flowable granular explosive comprising 2,6-bis(picrylamino)-3,5 dinitropyridine, at least 80 percent of said 2,6-bis(picrylamino)-3,5 dinitropyridine being in cubic particle form.

13. A flowable granular explosive comprising 2,6-bis(picrylamino)-3,5 dinitropyridine, at least 80 percent of said 2,6-bis(picrylamino)-3,5 dinitropyridine being in agglomerate particle form.

14. A flowable granular explosive comprising 2,6-bis(picrylamino)-3,5 dinitropyridine, at least 80 percent of said 2,6-bis(picrylamino)-3,5 dinitropyridine being in cubic or agglomerate particle form and mixtures thereof.

15. The explosive of claims 12, 13 or 14 wherein said particle form of 2,6-bis(picrylamino)-3,5 dinitropyridine is formed by removing the solvent from a solution of 2,6-bis(picrylamino)-3,5 dinitropyridine and dimethyl sulfoxide, said particle form of 2,6-bis(picrylamino)-3,5 dinitropyridine having greater bulk density and improved flow characteristics, thermal stability and sensitivity to shock stimulus than that of particles of 2,6-bis(picrylamino)-3,5 dinitropyridine prior to formation of said 2,6-bis(picrylamino)-3,5 dinitropyridine and dimethyl sulfoxide solution and removal of solvent therefrom.

16. The explosive of claim 15 wherein said particle forms of 2,6-bis(picrylamino)-3,5 dinitropyridine are in solid, crystalline form.

17. The explosive of claim 12 wherein said cubic form of 2,6-bis(picrylamino)-3,5, dinitropyridine is in discrete particle form.

* * * * *

UNITED STATES PATENT AND TRADEMARK OFFICE
CERTIFICATE OF CORRECTION

PATENT NO. : 4,564,405
DATED : January 14, 1986
INVENTOR(S) : Robert G. Pallanck It is certified that error appears in the above—identified patent and that said Letters Patent is hereby corrected as shown below:

Column 2, line 59 & 64 wherein the word "filteration" should read --filtration--.

Claim 7, lines 1-2 wherein the term "1, 2, 6-bis (picrylamino)-3, 5 dinitropyridine" should read --2, 6-bis (picrylamino)-3, 5 dinitropyridine--.

Claim 9, line 3 wherein the word "filteration" should read --filtration--.

Signed and Sealed this

Twenty-ninth Day of July 1986

[SEAL]

Attest:

DONALD J. QUIGG

Attesting Officer

Commissioner of Patents and Trademarks